United States Patent [19]

Benner et al.

[11] 4,256,669

[45] * Mar. 17, 1981

[54] PARA-AMINOPHENOL DERIVATIVES

[75] Inventors: Roland G. Benner, New Providence, N.J.; Paul D. Henson, Roanoke, Va.

[73] Assignee: Mallinckrodt, Inc., St. Louis, Mo.

[*] Notice: The portion of the term of this patent subsequent to Sep. 23, 1997, has been disclaimed.

[21] Appl. No.: 959,024

[22] Filed: Nov. 8, 1978

[51] Int. Cl.$^3$ .................. C07C 87/58; C07C 91/44
[52] U.S. Cl. ............................ 564/434; 564/435
[58] Field of Search ........................ 260/575, 576

[56] References Cited

U.S. PATENT DOCUMENTS

| | | | |
|---|---|---|---|
| 2,048,823 | 7/1936 | Semon | 260/809 |
| 2,053,785 | 9/1936 | Semon | 260/809 |
| 2,087,199 | 7/1937 | Clifford | 260/809 |
| 3,383,416 | 5/1968 | Benner | 564/418 |
| 3,418,373 | 12/1968 | Summers et al. | 260/576 |
| 3,432,460 | 3/1969 | Spacht | 525/6 |
| 3,717,680 | 2/1973 | Baron et al. | 260/575 |

*Primary Examiner*—Jacqueline V. Howard
*Attorney, Agent, or Firm*—Lawrence Rosen

[57] ABSTRACT

A process for the preparation of diaryl para-phenylenediamines from a crude para-aminophenol solution such as obtained by the catalytic hydrogenation of nitrobenzene in an aqueous acid reaction medium. The process comprises contacting the para-aminophenol containing acidic solution, after neutralization with ammonia, with an aromatic amine selected from the group consisting of aniline, mixed toluidines, ortho-toluidine, mixed xylidines, and mixtures thereof under conditions whereby the aromatic amine extracts the para-aminophenol from the crude feed solution and is separated therefrom. The separated solution comprised essentially of the aromatic amine extractant, para-aminophenol, and minor amounts of impurities is then contacted with an alkylation catalyst to produce the diaryl para-phenylenediamines.

19 Claims, No Drawings

PARA-AMINOPHENOL DERIVATIVES

The present invention relates to an improved process for the preparation of diaryl para-phenylenediamines from para-aminophenol. More particularly, the invention pertains to a process wherein para-aminophenol is separated from a crude solution thereof by use of an aromatic amine extractant and then reacting the extract of para-aminophenol and aromatic amines to produce diaryl para-phenylenediamines.

In recent years there has been an increasing demand for diaryl para-phenylenediamines which have been effectively used as rubber antioxidants and antiozonants, sometimes referred to as antidegradants. Prior art pertaining to this field include U.S. Pat. Nos. 2,048,823 (Semon); 2,053,785 (Semon); 2,087,199 (Clifford); and 3,432,460 (Spacht). The principal commercial method involves the reaction of hydroquinone with an aromatic amine or aromatic amine mixture in the presence of a condensation catalyst as described in U.S. Pat. No. 3,432,460. The hydroquinone reactant has however become quite expensive, and its cost has led to a substantial increase in the prices of the diaryl para-phenylenediamines.

Other methods have been proposed for the preparation of the diaryl para-phenylenediamines. For example, in U.S. Pat. No. 3,432,460 the hydroquinone is replaced by para-aminophenol, and the reaction with the aromatic amine in relatively large excess is carried out in the presence of alkylation catalysts such as iodine, metallic halides such as ferric chloride, etc.

A recently developed, and probably one of the most economical processes for making para-aminophenol involves the catalytic reduction of nitrobenzene with hydrogen in a dilute sulfuric acid solution in accordance with the teachings of U.S. Pat. No. 3,383,416 (Benner).

After removal of catalyst and unreacted nitrobenzene, the reaction mass consists of an aqueous solution containing up to about 12% para-aminophenol, up to about 4% aniline, up to about 18% sulfuric acid, and impurities. In order to isolate the para-aminophenol in a purified form, the solution is neutralized with ammonia and about one part of aniline is added for each part of para-aminophenol. The solution is then cooled to below 30° C. The resulting crystals of para-aminophenol are filtered from the aqueous ammonium sulfate solution and the aniline containing the impurities. The crystals are washed with aniline, then toluene and finally with dilute sodium bisulfite solution and then dried in a vacuum drier. The upper layer of aniline in the filtrate is separated from the lower layer of aqueous ammonium sulfate solution. The aniline is recovered by distillation. The ammonium sulfate solution can be used as a fertilizer after treatment to remove impurities which include small amounts of dissolved para-aminophenol.

Although the cost of nitrobenzene as a starting material for making para-aminophenol in accordance with the Benner Patent is relatively low, the cost of the finished para-aminophenol is relatively high because of the labor and equipment required in the many steps such as purification, crystallization, filtration, and drying involved in its isolation from the reduction mass. In addition, some losses of para-aminophenol occur in each step.

In accordance with the present invention, a method has been discovered whereby diaryl-phenylenediamines can be prepared economically from para-aminophenol that has been extracted from crude solutions thereof, e.g. the aqueous solution obtained by the catalytic hydrogenation of nitrobenzene. One aspect of the present invention is the discovery that the impurities normally associated with such crude para-aminophenol will not interfere deleteriously in the conversion of the para-aminophenol by reaction with aromatic amines to form the desired diarly para-phenylenediamine products. Secondly, it was discovered that the para-aminophenol could be extracted in high yields from its crude solution by utilizing aromatic amines such as, for example, aniline, mixed toluidines, ortho-toluidine, mixed xylidines, and mixtures of these amines. The resulting extract could then be pumped directly to a reactor, which will contain the usual alkylation catalyst, for making the diaryl para-phenylenediamines. At first this proposal did not appear feasible because the solubility of para-aminophenol in aniline was found to be only 8.0 grams of para-aminophenol per 100 grams of aniline at 90° to 91° C. This is equivalent to 14.6 mols of aniline per mol of para-aminophenol. Such a large excess of amine would make the procedure unwieldy because of the size of equipment required and the large amount of amine that would have to be recovered and recycled. However, an unexpected result was obtained when aniline was added to a hot slurry of para-aminophenol. It was found that a distinct separate upper layer of para-aminophenol and aniline formed with less than 2.0 mols of aniline per mol of para-aminophenol and that most of the para-aminophenol was in the upper layer. It is believed that the above finding represents an advance in the art of making the diaryl p-phenylenediamines in that it significantly decreases the cost of para-aminophenol as a starting material. The preferred aromatic amines are aniline, mixed toluidines, mixed xylidines, and mixtures of these amines.

The method of the present invention is particularly applicable to the crude para-aminophenol reaction product mixture obtained in the practice of the Benner Patent (i.e. U.S. Pat. No. 3,383,416) wherein an aqueous acidic reaction medium resulting from the catalytic hydrogenation of nitrobenzene is employed as the starting material. The Benner Patent is incorporated herein by reference. According to the present invention, the aqueous acidic solution is separated from unreacted nitrobenzene and neutralized with ammonia and then contacted with the aromatic amine extractant. The pH of the solution is raised to about 6.6 to 9.0 and preferably from about 7.0 to 7.4 during the neutralization.

As previously mentioned the aromatic amine extractant may be aniline, ortho-toluidine, mixed toluidines, mixed xylidines, or mixtures thereof. It will be understood isomeric mixtures of xylidines and toluidines may be employed. By mixed toluidines is meant the mixture of isomers obtained by the reduction of mixed nitrotoluenes prepared by the nitration of toluene, and by mixed xylidines is meant the mixture of isomers obtained by the reduction of mixed nitroxylenes prepared by the nitration of mixed xylenes. The amount of the aromatic amine extractant will generally range from about 2 to 9 mols per mol of para-aminophenol present in the crude feed material, and preferably from about 3 to 4 mols per mol of para-aminophenol. The extraction will be ordinarily carried out so that there are at least 3, preferably at least 4 stages of a continuous extraction system, to ensure that the extraction is substantially quantitative. In general, the extraction will be carried out in an continuous manner well known to the art. However, the same results can be accomplished by batchwise extraction.

An important aspect of the present invention has been the discovery that the crude feed material comprising an aqueous solution containing the para-aminophenol when contacted with an aromatic amine forms a solution of para-aminophenol and aniline much higher in concentration than would be expected based on the solubility of pure para-aminophenol in aniline. As discussed above, this discovery permitted the effective use of smaller amounts of the aromatic amine extractant than would have been expected. If greater amounts had been required, the entire process would have been considerably less feasible from an economic standpoint. The extraction is effectively carried out at temperatures from about 50° to 100° C., preferably from about 75° to 95° C.

In addition to the aromatic amine extractant the resulting extract will contain the para-aminophenol and may contain minor amounts of impurities or by-products such as aniline, p-aminodiphenylamine, p-hydroxydiphenylamine, and 4,4'diaminodiphenylether. Oxidation and reduction derivatives of the foregoing may also be present. Another advantage resulting from the recovery of para-aminophenol according to the present invention is that impurities such as p-aminodiphenylamine and p-hydroxydiphenylamine also form the desired diaryl para-phenylenediamines by further reaction with the aromatic amine.

Following recovery of the extract it may be sent either directly to storage or to a reactor wherein it is contacted with an alkylation or condensation catalyst at a temperature of from about 100° C. to 325° C., preferably from about 185° to 250° C., and at pressures ranging from atmospheric to 100 psig. As is usual for this reaction, the apparatus is designed to effect the continuous removal of water as it is formed from the reaction product mixture. The alkylation or condensation catalyst is selected from the group consisting of iodine, ferric chloride, ferric hydroxide sulfanilic acid, copper sulfate, copper chromite, phosphoric acid, alkyl phosphates, alkylphosphites, aniline halides, ammonium halides, etc. Only catalytically effective amounts of such condensation catalysts need be employed.

The alkylation or condensation reaction may be carried by either one-or two-steps conversion processes. In either process the reaction proceeds by the initial formation para-hydroxydiphenylamine which is then converted to the diaryl para-phenylenediamines. For certain procedures the first step may be carried out with sulfanilic acid as the catalyst, while ferric chloride is used in the second step. In other procedures, these catalysts have been used alone or in an admixture. U.S. Pat. No. 2,503,712 describes a two-step procedure using triethyl phosphate as a catalyst.

The resulting diaryl para-phenylenediamine products may be recovered from the reaction product mixture by vacuum distillation, preferably after destroying the catalyst. The distilled products are good antidegradants for rubber and neoprene used mainly as antioxidants, but those made from the toluidine and xylidines also have value as antiozonants. However, for use in rubber tires they are usually used in conjunction with antiozonants like the n-alkyl n-aryl-p-phenylenediamines. During vacuum distillation a forecut of unreacted para-hydroxydiphenylamine is obtained and is recycled. Then the diaryl-p-phenylenediamine is distilled from higher boiling products which remain as a residue. It has been found that these residues also have value as antioxidants, and for most purposes it is not necessary to remove the residue for commercial use, especially for use in black rubber such as in tires.

As previously mentioned, the process of the present invention may be carried out in a continuous or batchwise manner involving the sequential steps discussed in detail above. In contrast to the known process wherein solid or separated para-aminophenol is fed to the reaction zone along with the aromatic amine reactant, the present process involves the use of a liquid feed solution which contains not only the para-aminophenol but the aromatic amine as well. The latter material functions in two separate and distinct manners. Firstly, the aromatic amine is used to extract the para-aminophenol from a crude aqueous solution thereof. Secondly, the aromatic amine reacts with the para-aminophenol in a subsequent step, and without any intermediate separation, with the para-aminophenol in the presence of a condensation catalyst to form the desired diaryl para-phenylenediamines.

Typical diaryl para-phenylenediamines which can be produced in accordance with the process of the present invention included, but are not limited to, the following compounds and mixtures thereof:

N,N'-diphenyl-para-phenylenediamine
N,N'-ditolyl-para-phenylenediamine
N,N'-dixylyl-para-phenylenediamine
N-phenyl, N-tolyl-para-phenylenediamine
N-phenyl, N-xylyl-para-phenylenediamine
N-tolyl, N-xylyl-para-phenylenediamine, etc.

This invention is illustrated in greater detail by the example given below, although it is not intended in any way to limit the invention thereto.

EXAMPLE I

A solution which simulates the reaction mass obtained in the U.S. Pat. No. 3,383,416 by reduction of nitrobenzene after removal of catalyst and unreacted nitrobenzene was made up as follows:

| | |
|---|---|
| Para-Aminophenol (PAP) | 5.0 grams |
| Aniline | 1.3 grams |
| Sulfuric Acid (100%) | 6.5 grams |
| Water | 50.0 grams |

The solution was neutralized with anhydrous ammonia to a pH of 7.0 to 7.2. Set forth below are the minimum temperatures required to obtain a good separation of a top organic layer from the lower aqueous layer with various amounts of aniline including the aniline in the above solution:

| Mol Ratio Aniline: PAP | Temperature °C. |
|---|---|
| 1.5 | 90 to 95° |
| 4.3 | 80 to 85° |
| 7.3 | 75 to 80° |

EXAMPLE II

Using a neutralized solution as described in Example I, three extractions were made using 4.3 mols of aniline per mol of para-aminophenol in the first extraction and 4.02 mols of aniline in the second and third extractions. Each extract was analyzed for para-aminophenol and the following amounts of para-aminophenol were found in the aniline:

| Extraction | Temperature, °C. | % of Total PAP in Aniline |
|---|---|---|
| 1 | 80 to 85° | 68% |
| 2 | 50 to 60° | 24% |
| 3 | 50 to 60° | 6% |
| Total in 3 Extractions | | 98% |

The above results clearly show that the extraction of para-aminophenol would be almost quantative in a continuous countercurrent extraction unit with 3 or more stages, such as described by Scheibel, *Chem. Eng. Porcess*, volume 44, page 681–771 (1948).

EXAMPLE III (A) Using a commercial grade of para-aminophenol, comparative runs were carried out to compare the solubility at two different temperatures, of para-aminophenol in aniline as well as in commercial grades of mixed toluidines and xylidines with the following results:

Solubility of PAP in Aromatic Amines (g/100 g)

| | 30° C. | 90° C. |
|---|---|---|
| Aniline | 1.2 ± 0.1g* | 8.1 ± 0.6g |
| Toluidines (du Pont) | 1.3 ± 0.1g | 6.0 ± 0.2g |
| Xylidines (du Pont) | 1.0 ± 0.1g | 5.0 ± 0.2g |

*At 25° C.

(B) Using a neutralized solution as described in Example I, four extractions were made utilizing 4 mols of the aromatic amine per mol of para-aminophenol. Each extract was analyzed for para-aminophenol, and the results follow:

| Extraction | Aniline | Toluidines | Xylidines |
|---|---|---|---|
| 1 st | 3.40g (88° C.) | 2.91g (90° C.) | 3.26g (93° C.) |
| 2 nd | 1.25g (80° C.) | 1.11g (85° C.) | 0.86g (90° C.) |
| 3 rd | 0.31g (80° C.) | 0.58g (78° C.) | 0.55g (83° C.) |
| 4 th | | 0.32g (78° C.) | 0.25g (83° C.) |
| | 4.96g (99%) | 4.92g (98%) | 4.92g (98%) |

EXAMPLE IV (A) A 62.9 g sample of the crude para-aminophenol reaction product mixture obtained by the practice of the process of the U.S. Pat. No. 3,383,416 stripped of nitrobenzene but prior to neutralization, was neutralized with anhydrous ammonia to a pH of 7.0 to 7.2 and extracted with aniline as in Example II. The following amounts of para-aminophenol were found in the amine layers:

| Extraction | Temperature | Total PAP in Amine Layer |
|---|---|---|
| 1 | 85–90° C. | 4.72 g |
| 2 | 55–60° C. | 1.06 g |
| 3 | 55–60° C. | 0.31 g |
| Total in 3 Extractions | | 6.09 g |

(B) Aniline (5 g) was added to a 62.9 g. sample of the crude para-aminophenol feed of Run (A) prior to neutralization with anhydrous ammonia to a pH of 7.0 to 7.2. The mixture was allowed to cool to 25° C. and filtered. The filter cake was washed with 1 g. aniline, 1.5 g. toluene, twice with 1.25 g. cold water, and dried under a vacuum. A total of 5 g. of PAP was recovered.

Comparison of (A) and (B) above shows that considerably more para-aminophenol is recovered by the extraction procedure of the present invention.

EXAMPLE V

Para-aminophenol was extracted from 251.6 g. of the para-aminophenol reduction mass as described in Example IV. The three aniline extracts were combined and the aniline solvent removed under reduced pressure. The residual solid mass was then combined with 55.8 g. of aniline and 3.0 g. of ferric chloride hexahydrate in a reaction flask and heated to 200° to 210° C. for 3 hours during which time the water in the catalyst and ammonia from the reaction were distilled from the reaction mixture. The reaction temperature was then increased to 250° to 260° C., some aniline as well as water from the reaction distilled during the process, and maintained at this temperature for 15 hours. The reaction mixture was then allowed to cool to 110°–120° C. as 5.4 g. of a 25% aqueous sodium hydroxide solution was added to degrade the catalyst. The mixture was diluted with 50 g. of aniline, then was heated to distill the water added from the reaction mixture and filtered while hot to remove the iron salts. The reaction mixture was concentrated under reduced pressure and vacuum distilled to give 33 g. of high grade N,N'-diphenyl-p-phenylenediamine (DPPD), b.p. 205°–230° C. (0.4 mm Hg), m. p. 143°–147° C.

EXAMPLE VI

In a manner described in Example V for the reaction of para-aminophenol and aniline, except that the reaction at 250°–260° C. was for 8 hours rather than 15 hours, para-aminophenol (21.8 g, 0.2 mol) and mixed toluidines (64.2 g, 0.6 mol) were condensed in the presence of 3.0 g. of the hydrated ferric chloride. Vacuum distillation at 200°–220° C. gave a fraction which was predominately the N,N'-ditolyl para-phenylenediamines (33 g.).

EXAMPLE VII

In these experiments para-aminophenol was recovered from a commercial para-aminophenol reaction product mixture (U.S. Pat. No. 3,383,416) and converted to diaryl para-phenylenediamines by condensation with aromatic amines.

A. Isolation of PAP from its Reduction Mass.

General Procedure

Samples (251.6 g.) estimated to contain approximately 20 g. (8% by weight of PAP) of the reduction mass were neutralized with anhydrous ammonia to a pH of 7.0 to 7.2. The precipitated PAP was isolated by various techniques as described below. Results of several representative experiments are reported in Table 1.

(1) Simulated Commercial Process

Aniline (20 g., 1 g/g PAP) was added to the reduction mass sample prior to neutralization. The neutralized mixture was allowed to cool to 24° C. then was filtered. The purple filter cake was washed with aniline (4 g) toluene (6 g), and twice with ice water (2×5 g) then dried to give a gray powder.

(2) Aniline Extraction - 3×68.6 g. (Approx. 3×4 moles/mole PAP)

The neutralized reduction mass sample was extracted three times with 68.6 g. portions of aniline by heating the mixture until two distinct phases were observed and then separating the organic phase. The three extractions were performed at 86°, 60° and 60° C., respectively. The extracts were combined and concentrated under a vacuum. The recovered solid was washed twice with 5 g. portions of ice water and dried.

(3) Aniline Extraction - 4×33 g. (Approx. 4×2 moles/mole PAP)

The neutralized sample was extracted with 4×33 g. portions of aniline as previously described. The four extractions were performed at 86°, 73°, 60° and 45° C., respectively. The crude PAP was recovered, washed, and dried as outlined above.

TABLE 1

PAP RECOVERED FROM REDUCTION MASS SAMPLES (251.6 g.) BY VARIOUS ISOLATION TECHNIQUES

| Isolation Technique | Simulated Commercial Process | Aniline Extraction | |
|---|---|---|---|
| | | 3 × 68.6g | 4 × 33g |
| Quantity Recovered | 21.1 g | 24.2 g | 23.8 g |
| M.P., °C. | 179–182 | 175–177 | 178–180 |
| Relative Yields | 1.00 | 1.15 | 1.13 |

B. Condensation of PAP with Aniline in the Presence of Ferric Chloride.

General Procedure

Crude samples of PAP were isolated as described under Example VII and were reacted with aniline in the presence of ferric chloride according to the procedure described under Example V.

Vacuum distillation (0.2–0.4 mm Hg) gave a forerun (mostly aniline) to 110° C.; a para-hydroxy-diphenylamine (HDPA) fraction at 110° to 200° C.; a N,N'-diphenyl;-p-phenylenediamine fraction at 200° to 230° C.; and a non-distillable residue.

The reaction conditions and results of the three condensation experiments are reported in Table 2.

TABLE 2

CONDENSATION OF PAP WITH ANILINE IN THE PRESENCE OF FERRIC CHLORIDE CATALYST

| Experiment | 1 | 2 | 3 |
|---|---|---|---|
| PAP-Amount Used- g. (moles) | 21.1 (0.19) | 24.2 (0.22) | — |
| Other Reagents | | | |
| Aniline - g. (moles) | 108 (1.16) | 124 (1.33) | 132 (1.42) |
| FeCl$_3$ . 6H$_2$O - g. | 3 | 3 | 5 |
| Reaction Time (hrs) | | | |
| at 180°–200° C. | 18 | 18 | 17 |
| at 240°–260° C. | 5 | 5 | 5 |
| Distillation Products | | | |
| HDPA Fraction - g. | 5.3 | 4.4 | 4.5 |
| (Relative Recovery) | (1.00) | (0.83) | (0.85) |
| DPPD Fraction - g. | 26.4 | 29.7 | 29.4 |
| (Relative Recovery) | (1.00) | (1.13) | (1.11) |
| Residue - g. | 11.7 | 13.0 | 13.3 |
| M.P. °C. | 110–120 | 105–120 | — |
| (Relative Recovery) | (1.00) | (1.11) | (1.14) |

EXAMPLE VIII

Para-aminophenol was extracted from a 251.6 g. sample of its reduction mass with 2×40 g. samples of a 1:1 molar mixture of aniline and mixed toluidines as described previously.

The first extraction was performed at 90°–95° C., and the second at 35°–40° C. The combined extracts (mol ratios of aryl amines to PAP were approximately 0.4+0.4 to 0.2) were added to 3 g. of ferric chloride hexahydrate in a reaction vessel and heated at 190°–200° C. for 18 hours, then at 240°–260° for 6 hours. After the usual reaction work-up, vacuum distillation (0.4 mm Hg) gave 6.9 g of a p-hydroxydipenylamine fraction (b.p. 120°–205° C.), 30 g. of a diaryl p-phenylenediamine fraction (b.p. 205°–245° C., m.p. 70°–110° C.), and 17 g. of residue (m.p. 128°–142° C.).

The above examples involving the condensation reactions merely illustrate the invention. Much higher yields of the diaryl-p-phenylenediamines based on para-aminophenol are obtained by recycle of the recovered amines and the unreacted para-hydroxydiphenylamine. Also the distillation residue contains considerable product which can be recovered by known distillation techniques on a larger scale.

The above examples and data demonstrate that the improved process of this invention has the advantage of providing a relatively low cost solution of para-aminophenol in an aromatic amine which can be reacted directly in the presence of an alkylation or condensation catalyst to produce the desired diaryl para-phenylenediamines. Not only are expensive intermediate separation and purification steps eliminated, but it has been further shown that the impurities present in the crude para-aminophenol starting material do not adversely affect the reaction between the para-aminophenol and the aromatic amine. Moreover, the impurities do not impair the usefulness of the diaryl para-phenylenediamine products.

It will be understood that, although crude para-aminophenol solution utilized in the process of this invention is preferably derived by the reduction of nitrobenzene with hydrogen in an acid solution, e.g. sulfuric acid solution as described in the Benner Patent; crude para-aminophenol derived from other processes may be utilized by introducing such material into an aqueous acidic solution and then carrying out the process as set forth above. The acidic solution can be a mineral acid such as sulfuric acid or hydrocholoric acid and the like or a low molecular weight organic acid such as acetic acid and the like. In an alternative embodiment crude p-aminophenol wet cake or crude dry p-aminophenol is admixed with aromatic amine and water. When carrying out this latter procedure no adjustment in pH is made during the treatment.

While particular embodiments of this invention are shown above it will be understood that the invention is obviously subject to variations and modifications without departing from its broader aspects. Thus, the step of extracting the para-aminophenol from crude solutions thereof by utilizing aromatic amines may be utilized in a process directed primarily to the purification of para-aminophenol or in a process for converting the para-aminophenol to derivatives other than diaryl para-phenylenediamines.

What is claimed is:

1. A method for extracting para-aminophenol with aromatic amines from a crude aqueous solution of para-aminophenol made by the reduction of nitrobenzene, which comprises contacting the crude aqueous solution with at least a sufficient amount of an aromatic amine to extract the crude para-aminophenol therefrom, and then contacting the resulting extract with a condensation catalyst to form the corresponding diaryl para-phenylenediamines.

2. The method of claim 1 wherein the pH of the crude aqueous solution is initially adjusted to a pH of 6.6 to 9.0 and then heated to a temperature within the range of 50° to 100° C.

3. The method of claim 1 wherein the para-aminophenol is extracted with an aromatic amine in a mol ratio of from about 2 to 9 mols of the aromatic amine per mol of para-aminophenol.

4. The method of claim 1 wherein the resulting extract is contacted with the condensation catalyst at a temperature of from about 100° to 325° C.

5. The method of claim 1 wherein the crude aqueous acidic solution is prepared by the catalytic hydrogenation of nitrobenzene in aqueous sulfuric acid.

6. The method of claim 1 wherein the aromatic amine is selected from the group consisting of aniline, mixed toluidines, mixed xylidines, ortho-toluidine, or mixtures thereof.

7. The method of claim 1 wherein the aromatic amine is aniline.

8. The method of claim 1 wherein the aromatic amine is mixed xylidines.

9. The method of claim 1 wherein the aromatic amine is mixed toluidines.

10. The method of claim 1 wherein the extraction is carried out so that there are at least 3 transfer units.

11. The method of claim 1 wherein the condensation catalyst is ferric chloride.

12. The method of claim 1 wherein the condensation catalyst is sulfanilic acid.

13. A method for the preparation of diaryl para-phenylenediamines from a crude neutralized aqueous feed solution containing para-aminophenol which comprises the following sequential steps:
(a) extracting the para-aminophenol from the crude aqueous feed solution, maintained at a temperature of from about 50° to 100° C., by contacting it with an aromatic amine selected from the group consisting of aniline, mixed toluidines, mixed xylidines, ortho-toluidine, and mixtures thereof, the amount of aromatic amine ranging from about 2 to 9 mols per mols of para-aminophenol;
(b) recovering an extract solution comprising said para-aminophenol and said aromatic amine;
(c) passing said extract solution to a reaction zone where it contacts a condensation catalyst at a temperature of from about 100° to 325° C. whereby the para-aminophenol and the aromatic amine react and form corresponding diaryl para-phenylenediamines; and
(d) recovering the diaryl para-phenylenediamines from the resulting reaction product mixture.

14. The method of claim 13 wherein the pH of the crude feed solution ranges from about 7.0 to 7.4.

15. The method of claim 13 wherein the crude feed solution is obtained from the catalytic hydrogenation of nitrobenzene in aqueous sulfuric acid.

16. The method of claim 13 wherein the aromatic amine is aniline.

17. The method of claim 13 wherein the aromatic amine is mixed xylidines.

18. The method of claim 13 wherein the aromatic amine is mixed toluidines.

19. The method of claim 13 wherein the extraction is carried out so that there are at least 3 transfer units.

* * * * *

UNITED STATES PATENT AND TRADEMARK OFFICE
CERTIFICATE OF CORRECTION

PATENT NO. : 4,256,669
DATED : March 17, 1981
INVENTOR(S) : Roland G. Benner and Paul D. Henson It is certified that error appears in the above—identified patent and that said Letters Patent is hereby corrected as shown below:

Column 8, line 5 cancel "p-hydroxydipenylamine" and insert -- p-hydroxydiphenylamine --.

Signed and Sealed this

Eighth Day of September 1981

[SEAL]

Attest:

GERALD J. MOSSINGHOFF

Attesting Officer

Commissioner of Patents and Trademarks